United States Patent [19]
Levine et al.

[11] Patent Number: 6,007,990
[45] Date of Patent: Dec. 28, 1999

[54] DETECTION AND QUANTIFICATION OF ONE OR MORE NUCLEOTIDE SEQUENCE TARGET ANALYTES IN A SAMPLE USING SPATIALLY LOCALIZED TARGET ANALYTE REPLICATION

[76] Inventors: Robert A. Levine, 31 Pilgram La., Guilford, Conn. 06437; Stephen C. Wardlaw, 191 N. Cove Rd., Old Saybrook, Conn. 06475

[21] Appl. No.: 08/841,267

[22] Filed: Apr. 29, 1997

[51] Int. Cl.⁶ .............................. C12Q 1/68; C12P 19/34
[52] U.S. Cl. ................................. 435/6; 435/91.2
[58] Field of Search ..................... 435/6, 91.2; 536/24.3, 536/24.33; 935/77, 78

[56] References Cited

U.S. PATENT DOCUMENTS

| | | | |
|---|---|---|---|
| 4,711,955 | 12/1987 | Ward et al. | 536/29 |
| 5,328,824 | 7/1994 | Ward et al. | 435/6 |
| 5,604,097 | 2/1997 | Brenner | 435/6 |
| 5,616,478 | 4/1997 | Chetverin et al. | 435/91.2 |

FOREIGN PATENT DOCUMENTS 9321511  11/1993  WIPO .

OTHER PUBLICATIONS

Maniatis et al. Molecular Cloning, A Laboratory Manual, Cold Spring Harbor Lab., 1982, p. 161.

Fahy et al; "Self Sustained Replication (3SR): An Isothermal Transcription–Based Amplification System Alternative to PCR"; PCR Methods and Applications; pp. 25–33; (1991).

Chetverina et al; "Cloning of RNA Molecules in Vitro"; Nucleic Acids Research; pp. 2349–2353 (1993).

Burg et al; "Real–Time Fluorescence Detection of RNA Amplified by Qβ Replicase"; *Analytical Biochemistry*; 230; pp. 263–272 (1995).

*Primary Examiner*—Lisa B. Arthur
*Attorney, Agent, or Firm*—William W. Jones

[57] ABSTRACT

A target analyte which may be found in a substance, such as a biological or environmental substance, is assayed by inoculating a media with a sample of the substance. The target analyte is a unique nucleotide sequence of the RNA or DNA of a suspect organism, or any nucleotide target, or a combination of nucleotide sequences thereof, which organism may be found in the substance. The media contains selected target analyte amplifiers which will result in the amplification of any target analytes which are present in the substance. The media may also contain one or more labeled analyte-specific materials (LASMs) which can migrate through the media. The nature of the media is such that it will support target analyte-copying but will not allow the target analyte to migrate extensively within the media. After the substance to be assayed is added to the media and any target analytes are amplified, the LASMs will migrate by diffusion to resultant target analyte units or colonies in the media, thereby creating intensely labeled localized areas in the media which can be visually or mechanically detected. Each of the intensely labeled areas in the media will be surrounded by low intensity label halos. The number of high intensity labeled sites in the media will be proportional to the concentration of target analytes in the substance.

24 Claims, 4 Drawing Sheets

```
                            SEQUENCE LISTING

<160> NUMBER OF SEQ ID NOS: 24

<210> SEQ ID NO 1
    <211> LENGTH: 25
    <212> TYPE: DNA
    <213> ORGANISM: virus HIV-1

<400> SEQUENCE: 1
gcactttaaa ttttcccatt agtcc                                         25

<210> SEQ ID NO 2
    <211> LENGTH: 20
    <212> TYPE: DNA
    <213> ORGANISM: virus HIV-1

<400> SEQUENCE: 2
cctgcgggat gtggtattcc                                               20

<210> SEQ ID NO 3
    <211> LENGTH: 40
    <212> TYPE: DNA
    <213> ORGANISM: virus HIV-1

<400> SEQUENCE: 3
ttgaatagtc ggttacttgt tgacactcgg cactttaaat                         40

<210> SEQ ID NO 4
    <211> LENGTH: 40
    <212> TYPE: DNA
    <213> ORGANISM: virus HIV-1

<400> SEQUENCE: 4
accgactatt gttgacactg cctgcgggat gtggtattcc                         40

<210> SEQ ID NO 5
    <211> LENGTH: 24
    <212> TYPE: DNA
    <213> ORGANISM: M. tubercle bacilus

<400> SEQUENCE: 5
acccaatcga attgccacac cccg                                          24

<210> SEQ ID NO 6
    <211> LENGTH: 24
    <212> TYPE: DNA
    <213> ORGANISM: M. tubercle bacilus

<400> SEQUENCE: 6
ggcgcgcgag gccggcaagt acgg                                          24
```

<210> SEQ ID NO 7
<211> LENGTH: 40
<212> TYPE: DNA
<213> ORGANISM: M. tubercle bacilus

<400> SEQUENCE: 7
agtcggttac ttgttgacac tcgacccaat cgaattgcca 40

<210> SEQ ID NO 8
<211> LENGTH: 40
<212> TYPE: DNA
<213> ORGANISM: M. tubercle bacilus

<400> SEQUENCE: 8
accgactatt gttgacactg cgcgaggccg gcaagtacgg 40

<210> SEQ ID NO 9
<211> LENGTH: 24
<212> TYPE: DNA
<213> ORGANISM: M. tubercle bacilus (INH resistant)

<400> SEQUENCE: 9
acccaatcga attgccacac cccg 24

<210> SEQ ID NO 10
<211> LENGTH: 26
<212> TYPE: DNA
<213> ORGANISM: M. tubercle bacilus (INH resistant)

<400> SEQUENCE: 10
gccgatcgat gaaccccgga ggttcc 26

<210> SEQ ID NO 11
<211> LENGTH: 40
<212> TYPE: DNA
<213> ORGANISM: M. tubercle bacilus (INH resistant)

<400> SEQUENCE: 11
agtcggttac ttgttgacac acccaatcga attgccacac 40

<210> SEQ ID NO 12
<211> LENGTH: 40
<212> TYPE: DNA
<213> ORGANISM: M. tubercle bacilus (INH resistant)

<400> SEQUENCE: 12
accgactatt gttgacactg cgatgaaccc cggaggttcc 40

<210> SEQ ID NO 13
<211> LENGTH: 27
<212> TYPE: DNA
<213> ORGANISM: virus HBV

<400> SEQUENCE: 13
ggtgaagcga agtgcacacg gaccggc 27

<210> SEQ ID NO 14
<211> LENGTH: 26
<212> TYPE: DNA
<213> ORGANISM: virus HBV

<400> SEQUENCE: 14
gctgggggag gagattaggt taaagg 26

```
<210> SEQ ID NO 15
<211> LENGTH: 40
<212> TYPE: DNA
<213> ORGANISM: virus HBV

<400> SEQUENCE: 15
agtcggttac ttgttgacac ggtgaagcga agtgcacacg                40

<210> SEQ ID NO 16
<211> LENGTH: 38
<212> TYPE: DNA
<213> ORGANISM: virus HBV

<400> SEQUENCE: 16
accgactatt gttgacactg gctgggggag gagattag                  38

<210> SEQ ID NO 17
<211> LENGTH: 20
<212> TYPE: DNA
<213> ORGANISM: Pneumocystis carinii

<400> SEQUENCE: 17
gatggctgtt tccaagccca                                     20

<210> SEQ ID NO 18
<211> LENGTH: 20
<212> TYPE: DNA
<213> ORGANISM: Pneumocystis carinii

<400> SEQUENCE: 18
gtgtacgttg caaagtactc                                     20

<210> SEQ ID NO 19
<211> LENGTH: 40
<212> TYPE: DNA
<213> ORGANISM: Pneumocystis carinii

<400> SEQUENCE: 19
agtcggttac ttgttgacac gatggctgtt tccaagccca               40

<210> SEQ ID NO 20
<211> LENGTH: 40
<212> TYPE: DNA
<213> ORGANISM: Pneumocystis carinii

<400> SEQUENCE: 20
acgtgtacgt tgcaaagtac gtgtacgttg caaagtactc               40

<210> SEQ ID NO 21
<211> LENGTH: 22
<212> TYPE: DNA
<213> ORGANISM: S. aureus (methicillin resistant)

<400> SEQUENCE: 21
aaaatcgatg gtaaaggttg gc                                  22

<210> SEQ ID NO 22
<211> LENGTH: 22
<212> TYPE: DNA
<213> ORGANISM: S. aureus (methicillin resistant)

<400> SEQUENCE: 22
agttctgcag taccggattt gc                                  22
```

-continued

```
<210> SEQ ID NO 23
<211> LENGTH: 40
<212> TYPE: DNA
<213> ORGANISM: S. aureus (methicillin resistant)

<400> SEQUENCE: 23
agtcggttac ttgttgacac aaaatcgatg gtaaaggttg                    40

<210> SEQ ID NO 24
<211> LENGTH: 40
<212> TYPE: DNA
<213> ORGANISM: S. aureus (methicillin resistant)

<400> SEQUENCE: 24
gctgggggag gagattagac agttctgcag taccggattt                    40
```

DETECTION AND QUANTIFICATION OF ONE OR MORE NUCLEOTIDE SEQUENCE TARGET ANALYTES IN A SAMPLE USING SPATIALLY LOCALIZED TARGET ANALYTE REPLICATION

TECHNICAL FIELD

This invention relates to a method and paraphernalia for detecting the presence or the absence of a target analyte in a substance sample; and quantifying the analyte when it is found to be present in the sample. The specimen being analyzed can be a biological substance; an environmental substance; a food stuff substance; or some other substance which can harbor the target analyte. The target analyte is a specific nucleotide sequence which is suspected of being in the substance being tested. The presence or absence of the suspect organism or target sequence can be determined by amplifying the target analyte with strand displacement amplification (SDA) or polymerase chain reaction (PCR) reagents. If a nucleotide sequence of RNA is the target analyte and SDA or PCR reagents are employed, it will be necessary to convert RNA to DNA by reverse transcription prior to the amplification step. Alternatively, target analyte RNA amplification methods, such as Qβ replicase or RNA-X amplifications, may, in certain cases, be used without transcription. The analysis can be performed in a gel or a semi-solid media which permits amplification of the target analyte, but restricts migration of the amplified target analyte so that the products of amplification will form stationary detectable target analyte colonies in the media. The colonies may be detected and counted by various techniques, including the use of detectable SDA or PCR primers; or target analyte-complementary specific nucleotide sequences; or the use of detectable intercalating probes such as ethidium bromide, acridine orange, SYBR green, and related products. Such probes are available from Molecular Probes, Inc. of Eugene, Oreg.

BACKGROUND ART

The analysis of specimens for the presence or absence of target bacterial analytes, wherein the specimen is placed on a sterile growth media, is well known. Various bacteria can be detected in this manner in water, food stuffs; and in sample biological specimens, such as urine, cerebrospinal fluid, pleural fluid, ascites, joint fluid, stool, and the like. This testing procedure relies on the ability of the target analytes to replicate in the growth media to the extent that visible colonies of the target analytes can be observed. The various types of bacteria can be differentially labeled so as to aid in the differentiation between different bacterial colonies which grow in the media. When this analytic procedure is employed, the time necessary to form detectable colonies can be as short as one day, and as long as several weeks.

J. L. Burg et al describe a real time fluorescence detection procedure of RNA amplified by Qβ replicase, in Vol. 230 of Analytical Biochemistry (pp 263–272) 1995, Academic Press, Inc. The aforesaid detection procedure is non-specific and requires a considerable amount of sample preparation in order to function properly. Additionally, the Burg et al procedure cannot be used to detect DNA in a sample, and cannot detect more than one RNA target at a time. Quantification of any amplified RNA is a function of the time delay between the beginning of the procedure and the presence of detectable fluorescence in the sample container.

It would be highly desirable to be able to detect the presence or absence of one or more replicable target nucleotide sequence analytes in a single test, and quantify the target analytes in a short period of time. It would likewise be desirable to be able to detect organisms which cannot replicate in acellular systems, and to detect DNA genomes thought to be present in most life forms.

DISCLOSURE OF THE INVENTION

This invention relates to a method and paraphernalia for detecting the presence or absence of one or more nucleotide targets in a sample. Detection of the nucleotide target is accomplished by amplifying a unique portion of the DNA or RNA sequence in a suitable viscous media so as to form relatively stationary colonies of the amplified nucleotide sequence in the media, and then detecting and counting any resultant nucleotide sequence colonies which may form in the media. The target analyte being detected is thus the amplified nucleotide sequences or sequences of the suspect life form. Diffusion of the formed target analyte colonies in the media is restricted relative to the diffusion of marker or probe reagents.

The media contains, or is combined with, target analyte-specific primers and suitable enzymes and reagents which will cause amplification of the specified nucleotide sequence in the target analyte DNA or RNA through the use of strand displacement amplification (SDA); or through the use of polymerase chain reaction (PCR), or any other amplification procedures such as single primer or primeness 3SR, and in certain cases, Qβ replicase RNA amplification. In certain cases, other amplification procedures as described in PCR Technology: *Principals and Amplifications for DNA Amplification*, Ehrlich, H. A. ed. 1989, Stockton Press, New York, may be used in performance of this invention. The result is the creation of localized high-density population colonies of the specified nucleotide sequence in the media. Segments of non-target genomes which are contained in the sample and are introduced into the media, and which are not replicated by the amplification step, will not multiply, nor will they be detected. The analysis is performed in a media which may also contain, or be combined with one or more labeled analyte-specific materials (LASMs). The LASMs include a synthetic nucleotide sequence that is complementary to a portion of the specific nucleotide sequence forming the target analyte and which specific nucleotide sequence has been amplified. The label may be a free dye or fluorophore, or one which is attached to the complementary synthetic nucleotide sequence. The LASMs are initially distributed homogeneously throughout the media. The LASMs, following the laws of diffusion in the media, will migrate through the media to the amplified nucleotide sequence colonies, and will bind to these nucleotide sequences thereby differentially highlighting the colonies relative to the remainder of the media. Low intensity labeled halos will form around each colony due to localized migration of LASMs toward the colonies, and at the center of each halo will be a high intensity peak corresponding to the labeled colony. Any unamplified molecules of DNA or RNA present on the media will be non-detectable by virtue of their low concentration, even if stained by acridine orange, ethidium bromide or other stains. In certain cases, the label may be attached to one or both of the oligonucleotide primers used for PCR or SDA amplification. In these cases, the primers will function as the LASMs. The use of a kinetic study of signal intensity can null out non-specific background signals such as may be caused by cellular debris, since such non-specific background signals will not significantly increase with amplification.

When a specimen sample is being assayed for the presence or absence of only one target analyte, the colonies may be detected by non-specific stains for DNA or RNA such as acridine orange or ethidium bromide. The reason for this is that these fluorophores are able to intercalate non-specifically into any amplified nucleotide sequence, when such is produced, and specificity is achieved by the specificity of the amplification primers without the need to link the fluorophore to complementary nucleotide sequences. In cases where the sample is being assayed for the presence of more than one target analyte, then more than one complementary nucleotide sequence may be linked to one or more different fluorophores in order to highlight any amplified nucleotide sequence colonies which form in the media and to determine their type.

In performing the analysis of this invention, it is important that the amplified nucleotide sequence of the selected target analyte DNA or RNA be of such a size, i.e., about 150 mer to about 500 mer, so that the copies will be unable to migrate rapidly within the media, and thus will remain relatively stationary within the media during the course of the analysis. It is likewise important that the selected LASMs be of such a size, i.e., about 18 mer to about 40 mer, so as to be sufficiently small so that they will be able to diffuse more rapidly than the amplified target analyte sequences within the media, and yet sufficiently long so as to possess the necessary specificity to the amplified nucleotide sequences. Ideally, a LASM of about 18 mer may be used. Additionally, two or more LASMs of appropriate size which are directed against different nucleic acid sequences in the amplified target analyte may be used for enhanced specificity. The media must of course also be of such a type that the amplification reagents including the probes can diffuse within the media sufficiently rapidly to allow amplification to occur more rapidly than the products of such amplification can diffuse away from the colony.

The sample is prepared for analysis by first lysing all of its cellular and organism components so as to release into solution all of the genetic material of the cellular and organism components of the sample, see: Maniatis, T., Fritsch, E. F., and Sambrook, J. (1987) *Molecular Cloning: A Laboratory Manual,* 2nd Ed., Cold Spring Harbor Press. A known volume of nucleotide-rich aliquot of the lysed sample is then introduced onto the media and evenly spread out over the media. If necessary, diffusion of the target analyte into the media could be augmented by vertical electrophoresis, and/or by reducing its size prior to analysis by restriction digestion or mechanical shearing. The genetic material, DNA and/or RNA of the target component of the sample is thus exposed to the amplifying materials in the media. A target nucleotide sequence on the exposed genetic material is thus amplified to the extent that colonies of copies of the target analyte will be formed on the media. Since the size of the target analyte, and thus the size of the copies, is relatively large, the amplified target analyte colonies will remain relatively stationary on the media. The LASMs, if not pre-incorporated in the media, will be added to the media after the amplification step and be relatively homogeneously distributed there over. The LASMs are sized so as to be able to migrate in or through the media. Therefore, the LASMs will then migrate to the target analyte colonies and will bind to the copies in the target analyte colonies. This binding will cause the colonies to emit a higher level of the label signal than surrounding areas in the media, and in fact, the immediately surrounding areas which border the colonies will emit a weakened label signal. The net result will be the formation of "bright" spots surrounded by "dim" halos in the media. In the event that there is no target analyte present in the sample, then the media will retain a relatively even level of label signal emission, and will appear to be evenly "colored". Detection of the binding of the complementary nucleotides containing a fluorophore to their respective target analytes may also be accomplished by time-resolved fluorescence as described in U.S. Pat. No. 5,485,530, Lokowicz et al. If desired, the sample could be applied to the media prior to cell lysis, so that the localization of the target with respect to cellular nucleotides may be ascertained, i.e., to determine whether the target is intracellular or extracellular. If desired, the LASMs, as well as the other reagents required for amplification, could be impregnated onto a solid support such as a nylon membrane or paper strip, and allowed to diffuse into the media by placing the membrane on top of the media.

The assay can be completed within several hours after inoculating the media with the sample by producing copies of the target analytes in the media. Viruses, bacteria, fungi, mycoplasma, protozoa, or specific nucleotides present in any type of cell or specimen can be assayed by using the specific nucleotide sequence-amplification and detection method of this invention, and since one knows the volume of the specimen sample added to the media, by counting the number of highlighted colonies in the media, one can detect the amount of target analyte per unit volume of the specimen sample, thus enabling the securement of a quantitative analysis of the sample for target analyte.

A portion of the media will be inoculated with a control sample containing no known target nucleotides, but treated and prepared exactly as the known sample. This portion of the media will serve as a negative control. In the event that amplified labeled colonies form in the negative control area of the media, one can presume contamination of the media or the amplification or lysing reagents, or all, and the results of the assay are invalid. Another portion of the media can also be segregated and used as a positive control by applying a sample containing a known amount of the target analyte(s) therein when the test is performed. If the positive control area of the media fails to have the appropriate number and type of colonies, then the amplification and/or detection steps of the assay are not functioning properly, and the assay is invalid.

It is therefore an object of this invention to provide a method and apparatus which can be used to assay a specimen sample for the presence or absence of a target analyte.

It is another object of this invention to provide a method and apparatus of the character described wherein the sample is placed on a media which is combined with a target analyte-specific labeled material that can migrate within the media.

It is a further object of this invention to provide a method and apparatus of the character described wherein the target analyte is a signature nucleotide sequence or sequences derived from RNA or DNA of a life form.

It is an additional object of this invention to provide a method and apparatus of the character described wherein the target analyte is detected by forming amplified colonies thereof, and by differentially labeling any amplified colonies which form in the media.

These and other objects and advantages of the invention will become more readily apparent from the following detailed description of the invention when taken in conjunction with the accompanying drawings, in which:

DETAILED EXAMPLE FOR CARRYING OUT THE INVENTION

Figure 1:
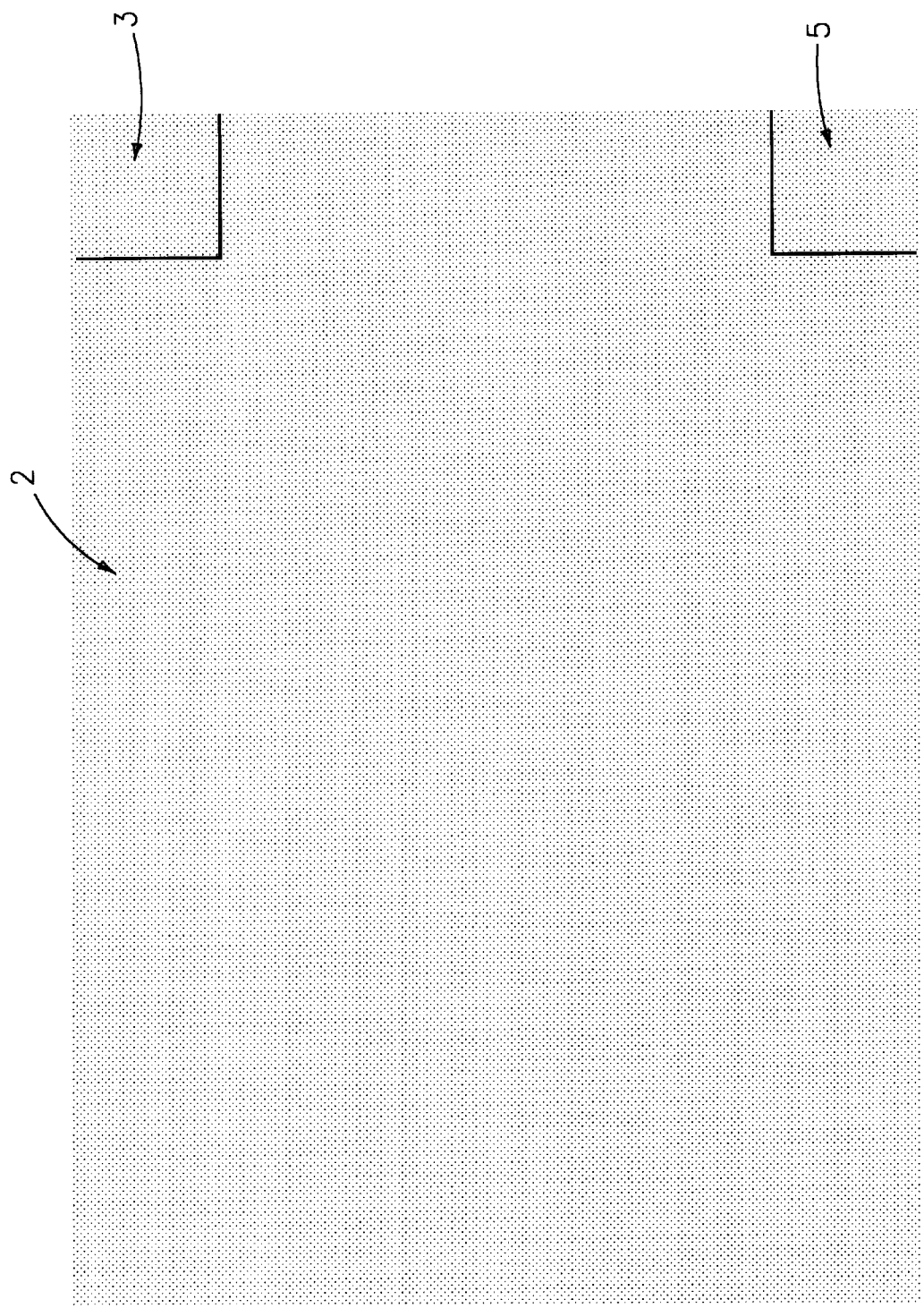
FIG. 1 is a plan view of a labeled target analyte-specific and growth media mixture formed in accordance with this invention.
Figure 2:
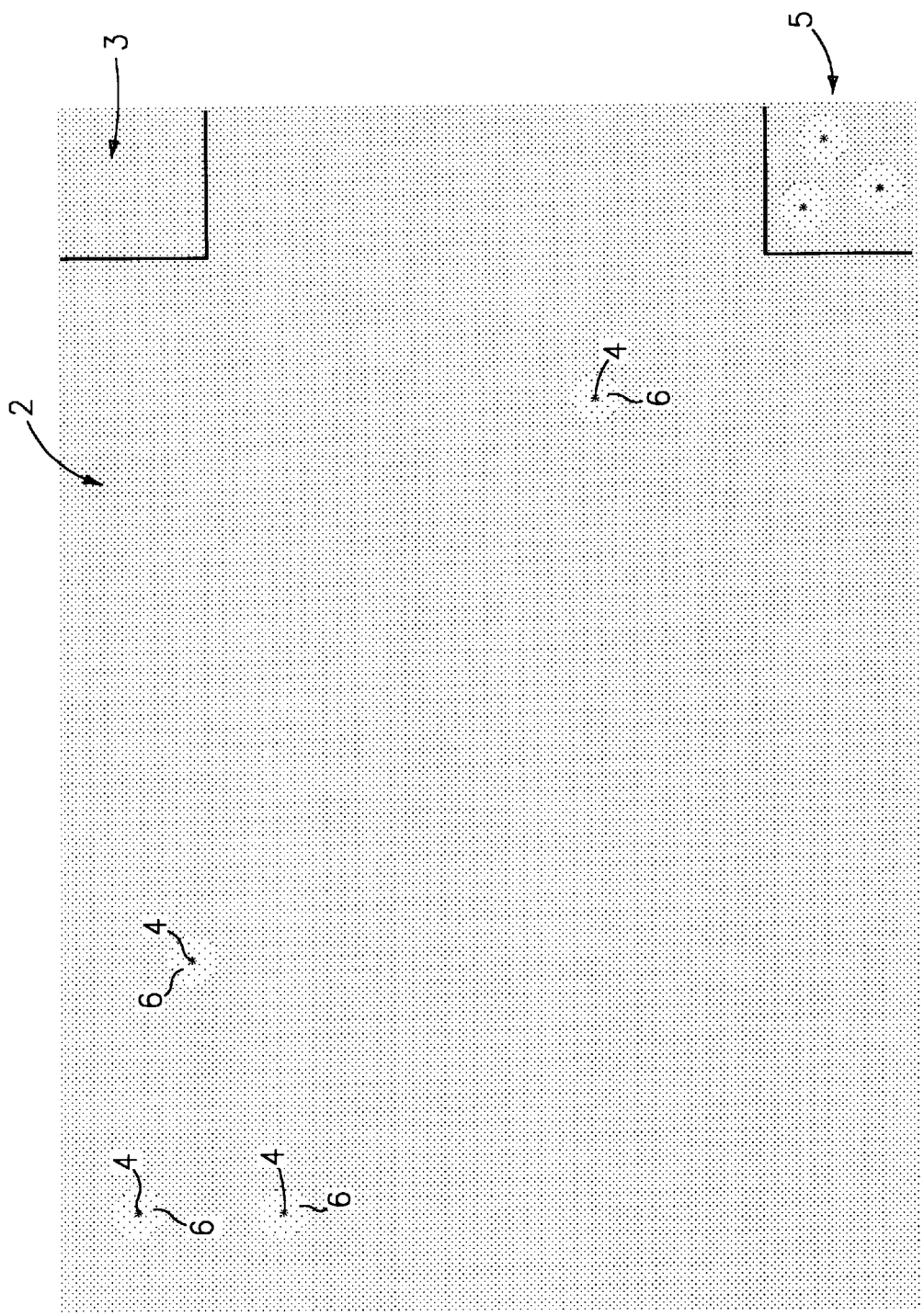
FIGS. 2 and 3 are plan views similar to FIG. 1 but showing the formation of varying degrees of localized intensely labeled areas in the mixture due to the presence of the target analyte in the sample being assayed.
Figure 3:
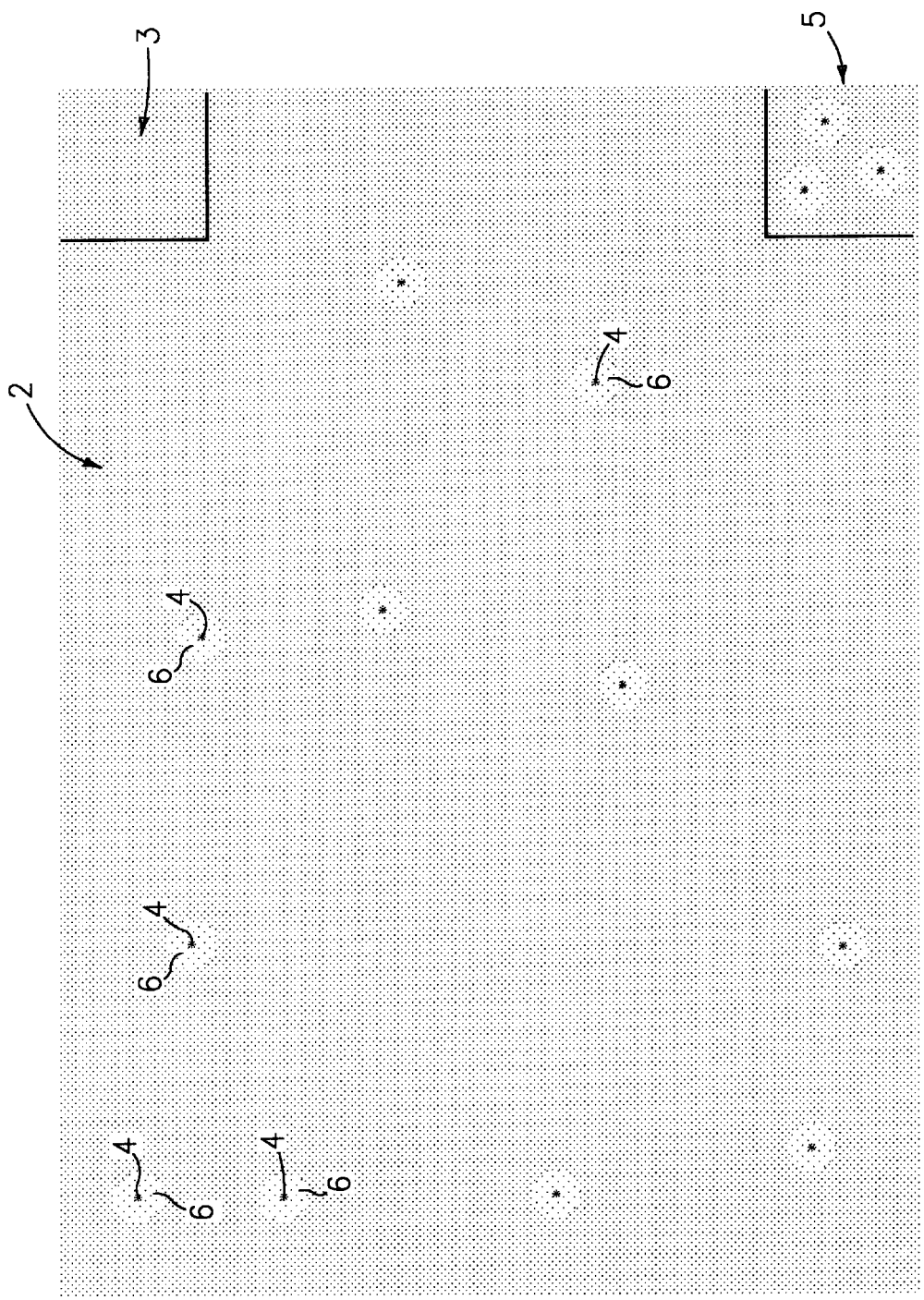

Referring now to FIG. 1, there is shown a plan view of a rectangular section of a media, denoted generally by the numeral 2, which is adapted for performing the method of this invention. The media field as shown in FIG. 1 is evenly shaded so as to indicate an evenly distributed label signal emission which will be detected by the human eye or by a scanning instrument either before the media has been inoculated with the sample; or after introduction and incubation of the sample, when there is no target analyte present in the sample. The area 3 in the media 2 is an area which will not be exposed to the sample being assayed, but which contains all of the reagents used in the test, and therefore serves as a negative control area. The area 5 in FIG. 1 is an area which also contains all of the reagents used in the test. The area 5 will not be exposed to the sample, but will be exposed to a positive control solution which contains a known concentration of the target analyte. FIGS. 2 and 3 are illustrative of the resulting change in the emission pattern in the media 2 when the target analyte is present in the sample. FIG. 2 shows the result of a relatively low level of target analyte in the sample which will produce a plurality of more highly labeled colonies 4 surrounded by halos 6 of lower level label in the media 2. FIG. 3 shows the result when there is a relatively high level of target analyte in the sample. It will be noted from FIGS. 2 and 3 that one can count the colonies 4, and since the volume of the sample inoculum and the size of the field of media 2 is known, one can derive a concentration of target analyte per unit volume by following the procedure of this invention. It will also be noted from FIGS. 2 and 3 that the positive control area 5 will have the same number of colonies irrespective of the number of colonies which form in the remainder of the media 2.

Figure 4:
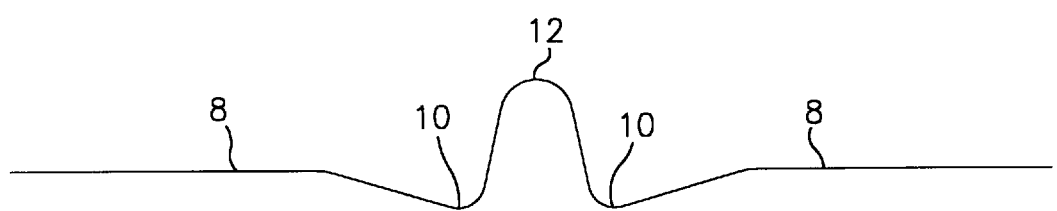
FIG. 4 is a pictographic trace of the signal intensity levels emanating from the sample as the latter is scanned by an automatic signal detection instrument.

FIG. 4 is a pictograph of the emission intensity from the label that will be detected by an auto-analyzing instrument as it performs a linear scan of the media. The trace 8 represents the emission level of the media per se; the dips 10 represent the low levels of emission in the halos 6; and the peak 12 represents the high level of emission in the colonies 4.

The following are examples of suspect organism-specific target analytes which can be detected utilizing the technique of this invention, and reagents for use in detecting each target analyte.

EXAMPLE 1

One organism that can be detected and quantified using the technique of this invention is the HIV-1 virus. A target analyte gene for detecting HIV-1 is viral polymerase, whose function is the replication of the viral genome. (It is noted that the polymerase gene is only one of several HIV-1 genes that could be detected with this method. In fact, a protocol that simultaneously quantifies the concentrations of two HIV-1 genes, for example, both polymerase and protease, would be susceptible to very few false positive results since the polymerase-to-protease ratio will be relatively constant.) A forward primer that can be used to amplify the viral polymerase gene using PCR is: SEQ. ID NO:1:

GCACTTTAAATTTTCCCATTAGTCC;

and a reverse primer is: SEQ. ID NO:2:

CCTGCGGGATGTGGTATTCC.

If a separate LASM is used, it will be complementary to some region between the aforesaid forward or reverse primers. The complementary nucleotide sequence can be attached covalently to a fluorophore which will provide the necessary emission signal. In this case the LASM should lack a hydroxyl group on the 3' position of the nucleotide at the 3' end of the oligonucleotide to inhibit amplification of the product resulting from hybridization of one LASM with another. If a separate LASM is not used, then the fluorophore will be attached to the 5' terminus of one or both of the oligonucleotide primers used for PCR or to one or more of the internucleoside linkages. All primers and LASMs should lack a hydroxyl group on the 3' position of the nucleotide at the 3' end of the oligonucleotide to inhibit amplification of the product resulting from hybridization of one LASM with another. Suitable media include acrylamide gels containing 2.5 to 5.0% acrylamide, and between 0.025 and 2.5% bis-acrylamide; or 0.5% agarose; and standard and low-melt agarose gels containing 0.75 to 1.5% agarose. As noted above, the technique of this invention is optimized by using media compositions with low gel percentages, for example about 4 to 5% for an acrylamide gel, and 2% or less for agarose.

A medium impregnated with the appropriate PCR reagents can be prepared as follows. A 100 ml wash solution consisting of 20 mM Tris, having a pH of about 8.0, in 50 mM EDTA; and a 10 ml storage solution consisting of 2 mM Tris, having a pH of about 8.0, in 0.5 mM EDTA are prepared. The gel is immersed in 5 ml of the wash solution for about 15 minutes at room temperature. This step is repeated 5 times in fresh wash solution. The gel is then immersed in 5 ml of the storage solution containing PCR primers, enzyme and dNTPs, and the like.

For amplification by the SDA method, related primers containing appropriate restriction sites will be used. For example, a forward primer that can be used to amplify the viral polymerase gene by SDA is: SEQ. ID NO:3:

TTGAATAGTCGGTTACTTGTTGACACTCGGCACTTTAAAT;

and a reverse primer is: SEQ. ID NO:4:

ACCGACTATTGTTGACACTGCCTGCGGGATGTGGTATTCC.

If a separate LASM is used, it will be complementary to some region between the aforesaid forward or reverse primers. The oligonucleotide-based LASM should not be complementary to either the forward or reverse primers, but be complementary to a portion of the target molecule. This act will specifically focus the detectable agent at the molecular colony, and not to primers that may be freely distributed throughout the media. The complementary nucleotide sequence can be attached covalently to one or more fluorophores which will provide the necessary emission signal(s). If a separate LASM is not used, then the fluorophore will be attached to the 3' terminus of one or both of the oligonucleotide primers used for SDA, or to one or more of the internucleoside linkages.

A medium impregnated with the appropriate SDA reagents can be prepared as follows. A 100 ml wash solution consisting of 50 mM potassium phosphate, having a pH of about 7.4 and 6 mM MgCl2; and a 10 ml storage solution consisting of the wash solution plus SDA primers, an appropriate restriction enzyme, exo-Klenow polymerase and dNTPs, is prepared. The gel is immersed in 5 ml of the wash solution for about 15 minutes at room temperature. This step is repeated 5 times in fresh wash solution. The gel is then immersed in 5 ml of the storage solution.

A LASM can be prepared as follows. For a dye-isothiocyanate label, the complementary nucleotide sequence strands will contain one or more modified bases carrying an appended primary amine. The strand to be labeled is dissolved in 0.1 M sodium bicarbonate having a pH of 9.0, and the dye-isothiocyanate is dissolved in dry DMF at a concentration of 10 mg/ml. The dye solution is then added drop wise to the complementary nucleotide sequence solution with stirring and the reaction incubated at room temperature for 12 hours. Free dye is then removed by gel filtration and the dye-complementary nucleotide sequence conjugate purified by gel electrophoresis or HPLC. For a dye-succinimidyl ester label, the complementary nucleotide sequence to be labeled is dissolved in 0.1 M sodium phosphate, having a pH of 8.0, and the complementary nucleotide sequence-label conjugating reaction is performed at 4° C. to minimize hydrolysis of the succinimidyl ester label. Various dye-labeled DNAs can be prepared directly by chemical synthesis and are widely used for DNA sequencing.

The target analyte can be embedded in the media in the following manner. A suspension of approximately $2.5 \times 10^7$ cells is prepared from a tissue homogenate or culture, and washed thoroughly in tissue culture medium (no fetal calf serum) or isotonic saline. The mixture is then centrifuged at 2,000 g for 20 minutes at 4° C., the supernatant is removed, and the nucleic acid-containing pellet is drained thoroughly. The cells are re-suspended in 5 mL of 50 mM Tris (pH 8.0) and 50 mM EDTA and frozen at −20° C. To the frozen solution is added 0.5 mL of lysozyme solution (10 mg/mL lysozyme in 0.25 M Tris (pH 8.0)) and the mixture incubated at 4° C. for 45 min. One milliliter of STEP solution (0.5% sodium dodecyl sulfate, 50 mM Tris (pH 7.5), 0.4 M EDTA, 1 mg/mL Proteinase K (added immediately before use) is added and the solution incubated at 50° C. for one hour. Six milliliters of buffered phenol is added and the emulsion centrifuged at 1,000 g for 15 minutes. The upper, nucleic acid-containing layer is transferred to a separate tube and 0.1 volume 3 M sodium acetate and 2 volumes absolute ethanol is added. The precipitate, containing DNA and RNA, is redissolved in 5 mL 50 mM Tris (pH 7.5) and 1 mM EDTA. If only cellular DNA is desired, 200 μg RNase A may be added. The nucleic acid may be applied directly to the media, or it may first be treated with a restriction enzyme or sheared with a needle to reduce its average size.

The target analyte-amplifying PCR reaction can be performed as follows. The gel, specimen sample, PCR and LASM mixture is heated to 95° C. for 3 minutes, and then 30 cycles of heating to 95° C. for 45 seconds, annealing at 55° C. for 90 seconds, and extending at 72° C. for 1 minute for every 750 nucleotides. For example, if one is amplifying a target that is 750 nucleotides long, that one would allow the extension reaction to proceed for 1 minute; on the other hand, if the target were 375 nucleotides long, the one would allow the extension to proceed for 30 seconds. The reaction is finished with a 10 minute extension at 72° C. The media is then examined to determine the presence or absence of target analyte colonies in the media.

The target analyte-amplifying SDA reaction can be performed as follows. The gel, specimen sample, SDA and LASM mixture is incubated at 37° C. for between thirty minutes and four hours. The media is then examined to determine the presence or absence of target analyte colonies in the media.

EXAMPLE 2

Another target analyte that can be detected and quantified using the technique of this invention is M. tuberculosis. The target gene for detecting M. tuberculosis is inhA whose function is fatty acid biosynthesis. The forward primer for amplification of inhA by PCR is SEQ. ID NO:5:

ACCCAATCGAATTGCCACACCCCG;

and the reverse primer is: SEQ. ID NO:6:

GGCGCGCGAGGCCGGCAAGTACGG.

These primers will amplify a 279 base pair region of the inhA gene in M. tuberculosis. If a separate LASM is used, it will be complementary to some region between the aforesaid forward or reverse primers. The oligonucleotide-based LASM should not be complementary to either the forward or reverse primers, but be complementary to a portion of the target molecule. This act will specifically focus the detectable agent at the molecular colony, and not to primers that may be freely distributed throughout the media. The media and LASM preparation procedures are essentially the same as set forth in Example 1, as is the introduction procedure.

For amplification of the inhA gene by SDA, a forward primer is SEQ. ID NO:7:

AGTCGGTTACTTGTTGACACTCGACCCAATCGAATTGCCA;

and the reverse primer is SEQ. ID NO:8:

ACCGACTATTGTTGACACTGCGCGAGGC-CGGCAAGTACGG.

If a separate LASM is used, it will be complementary to some region between the aforesaid forward or reverse primers. The media and LASM preparation procedures are essentially the same as set forth in Example 1, as is the introduction procedure.

EXAMPLE 3

A further organism that can be detected and quantified by using the technique of this invention is INH-resistant *M. tuberculosis*. The target analyte gene for detecting INH-resisistant *M. tuberculosis* is mutant inhA whose function is fatty acid biosynthesis. The forward primer for amplification of the mutant inhA gene by PCR is SEQ. ID NO:9:

ACCCAATCGAATTGCCACACCCCG;

and the reverse primer is SEQ. ID NO:10:

GCCGATCGATGAACCCCGGAGGTTCC.

These primers will amplify a 159 base pair region of the mutant inhA gene in INH-resistant *M. tuberculosis*. If a separate LASM is used, it will be complementary to some region between the aforesaid forward or reverse primers. The oligonucleotide-based LASM should not be complementary to either the forward or reverse primers, but be complementary to a portion of the target molecule. This act will specifically focus the detectable agent at the molecular colony, and not at primers that may be freely distributed throughout the media. The media and LASM preparation procedures are essentially as set forth in Example 1, as is the introduction procedure.

For amplification of the mutant inhA gene by SDA, a forward primer is SEQ. ID NO:11:

AGTCGGTTACTTGTTGACACACCCAATCGAATTGCCACAC;

and the reverse primer is SEQ. ID NO:12:

ACCGACTATTGTTGACACTGCGATGAACCCCGGAGGTTCC.

If a separate LASM is used, it will be complementary to some region between the aforesaid forward or reverse primers. The media and LASM preparation procedures are essentially the same as set forth in Example 1, as is the introduction procedure.

EXAMPLE 4

An additional organism that can be detected and quantified using the technique of this invention is HBV. The target gene for detecting HBV is pX gene whose function is transcription. The forward primer for amplification of the pX gene by PCR is SEQ. ID NO:13:

GGTGAAGCGAAGTGCACACGGACCGGC;

and the reverse primer is SEQ ID NO:14:

GCTGGGGAGGAGATTAGGTTAAAGG.

These primers will amplify a 196 base pair region of the pX gene in HBV. If a separate LASM is used, it will be complementary to some region between the aforesaid forward or reverse primers. The oligonucleotide-based LASM should not be complementary to either the forward or reverse primers, but be complementary to a portion of the target molecule. This act will specifically focus the detectable agent at the molecular colony, and not at primers that may be freely distributed throughout the media. The media and LASM preparation procedures are essentially as set forth in Example 1, as is the introduction procedure.

For amplification of the HBV pX gene by SDA, a forward primer is SEQ. ID NO:15:

AGTCGGTTACTTGTTGACACGGTGAAGC-
GAAGTGCACACG;

and the reverse primer is SEQ. ID NO:16:

ACCGACTATTGTTGACACTGGCTGGGGGAGGAGATTAG.

If a separate LASM is used, it will be complementary to some region between the aforesaid forward or reverse primers. The media and LASM preparation procedures are essentially the same as set forth in Example 1, as is the introduction procedure.

EXAMPLE 5

Another organism that can be detected and quantified using the technique of this invention is *Pneumocystis carinii*. The target analyte gene for detecting *Pneumocystis carinii* is mitochondrial rRNA whose function is protein synthesis. The forward primer for amplification of the *Pneumocystis carinii* mitochondrial rRNA gene is SEQ. ID NO:17:

GATGGCTGTTTCCAAGCCCA;

and the reverse primer is SEQ. ID NO:18:

GTGTACGTTGCAAAGTACTC.

These primers will amplify a 344 base pair region of the mitochondrial rRNA gene in *Pneumocystis carinii*. If a separate LASM is used, it will be complementary to some region between the aforesaid forward or reverse primers. The oligonucleotide-based LASM should not be complementary to either the forward or reverse primers, but be complementary to a portion of the target molecule. This act will specifically focus the detectable agent at the molecular colony, and not at primers that may be freely distributed throughout the media. The media and LASM preparation procedures are essentially as set forth in Example 1, as is the introduction procedure.

For amplification of the *Pneumocystis carinii* mitochondrial rRNA gene by SDA, a forward primer is SEQ ID NO:19:

AGTCGGTTACTTGTTGACACGATGGCTGTTTCCAAGCCCA;

and the reverse primer is SEQ ID NO:19:

ACGTGTACGTTGCAAAGTACGTGTACGTTGCAAAGTACTC.

If a separate LASM is used, it will be complementary to some region between the aforesaid forward or reverse primers. The media and LASM preparation procedures are essentially the same as set forth in Example 1, as is the introduction procedure.

EXAMPLE 6

An additional organism that can be detected and quantified using the technique of this invention is methicillin-resistant *S. aureus*. The target analyte gene for detecting methicillin-resistant *S. aureus* is mecA which is a penicillin binding protein. The forward primer for amplifying the mecA gene by PCR is SEQ. ID NO:21:

AAAATCGATGGTAAAGGTTGGC;

and the reverse primer is SEQ. ID NO:22:

AGTTCTGCAGTACCGGATTTGC.

These primers will amplify a 533 base pair region of the mecA gene. If a separate LASM is used, it will be complementary to some region between the aforesaid forward or reverse primers. The oligonucleotide-based LASM should not be complementary to either the forward or reverse primers, but be complementary to a portion of the target molecule. This act will specifically focus the detectable agent at the molecular colony, and not at primers that may be freely distributed throughout the media. The media and LASM preparation procedures are essentially as set forth in Example 1, as is the introduction procedure.

For amplification of the mecA gene by SDA, a forward primer is SEQ. ID NO:23:

AGTCGGTTACTTGTTGACACAAAATCGATGGTAAAGGTTG;

and the reverse primer is SEQ. ID NO:24:

GCTGGGGAGGAGATTAGACAGTTCTGCAGTACCGGATTT.

If a separate LASM is used, it will be complementary to some region between the aforesaid forward or reverse primers. The media and LASM preparation procedures are essentially the same as set forth in Example 1, as is the introduction procedure.

It will be appreciated that if a separate LASM is used, it can be complementary to any region between the forward and reverse primers. Specimen samples which can be analyzed by means of this invention include tissue, blood, biological fluids such as sputum for respiratory target analytes, stool for intestinal target analytes. Essentially the presence or absence, and quantification of any life form, including but not limited to, protozoa, bacteria, viruses, fungi, and the like can be detected in essentially any specimen sample by using the technology of this invention.

Likewise, different life forms, such as viruses and bacteria, to name two, can be detected and quantified in a single test which is performed on a common sample by following the precepts of this invention. Thus completely different causes of respiratory disease, diarrhea, genital disease, and many other diseases can be ascertained in a single test using the procedure of this invention.

Since many changes and variations of the disclosed embodiments of the invention may be made without departing from the inventive concept, it is not intended to limit the invention otherwise than as required by the appended claims.

What is claimed is:

1. An assembly for determining the presence or absence of a target nucleotide sequence analyte hereinafter referred to as target analyte, in a specimen sample, said assembly comprising:

a) a media into which the specimen sample can be introduced, and which is operable to support amplification of the target analyte to an extent needed to produce colonies thereof while limiting migration of any amplified target analyte colonies which are formed within the media;

b) target analyte-specific amplification reagents essentially homogeneously distributed throughout said media, said amplification reagents being operable to selectively amplify and form colonies of any of the target analyte which may be present in the specimen sample; and c) a labeled analyte-specific material (LASM) which will bind to said target analyte, said LASM being essentially homogeneously distributed throughout said media and capable of migrating through said media to an extent necessary to differentially highlight any amplified target analyte colonies which may be formed in said media.

2. The assembly of claim 1 wherein said LASM is sufficiently mobile in said media so as to be capable of forming high intensity labeled target analyte colony areas in said media, which areas are surrounded by lower intensity labeled zones in said media.

3. The assembly of claim 1 wherein said LASM is an artificial target analyte-specific nucleotide sequence which is complementary to said target analyte.

4. The assembly of claim 1 wherein said LASM is an intercalating agent which can intercalate into said target analyte.

5. The assembly of claim 1 wherein said amplification reagents are polymerase chain reaction reagents.

6. The assembly of claim 1 wherein said amplification reagents are strand displacement amplification reagents.

7. An assembly for determining the presence or absence of two or more different target nucleotide sequence analytes hereinafter referred to as target analytes, in a specimen sample, said assembly comprising:

a) a media into which the specimen sample can be introduced, and which is operable to support amplification of the target analytes to an extent needed to produce colonies thereof while limiting migration of any amplified target analyte colonies which are formed within the media;

b) target analyte-specific amplification reagents essentially homogeneously distributed throughout said media, said reagents being operable to selectively amplify and form colonies of any of the target analytes which may be contained in the specimen sample; and c) labeled analyte-specific materials (LASMs) which will bind selectively to said target analytes, said LASMs being essentially homogeneously distributed throughout said media and differentially labeled and being capable of migrating through said media to an extent necessary to differentially highlight any amplified target analyte colonies which may be formed in said media whereby any colonies of one of the target analytes which form will be distinguishable from any colonies of another of the target analytes which form in the media.

8. The assembly of claim 7 wherein said LASMs are sufficiently mobile in said media so as to be capable of forming high intensity labeled target analyte colony areas in said media, which areas are surrounded by lower intensity labeled zones in said media.

9. The assembly of claim 7 wherein said LASMs comprise respective differentially labeled artificial nucleotide sequences which are complementary to respective sequences of said target analytes.

10. The assembly of claim 7 wherein said amplification reagents are polymerase chain reaction reagents.

11. The assembly of claim 7 wherein said amplification reagents are strand displacement amplification reagents.

12. A method for determining the presence or absence of a target nucleotide sequence hereinafter referred to as target analyte, in a specimen sample, said method comprising the steps of:

a) providing a specimen sample to be analyzed;

b) providing a testing media suitable for specimen sample introduction, said testing media containing target analyte-specific amplification materials which are essentially homogeneously distributed throughout said media;

c) releasing any of said target analyte from target organisms which may be contained in the specimen sample;

d) reacting any released target analyte with said target analyte-amplification material in said media so as to form essentially immobile amplified colonies of said target analyte in said media; and e) reacting any released target analyte with a labeled analyte-specific material (LASM)_ which is substantially homogeneously distributed throughout said testing media and which can migrate through said testing media, said detectable substance being operable to bind with amplified target analyte units in any formed target analyte colonies in said media so as to differentially highlight said target analyte colonies from the remainder of said media.

13. The method of claim 12 wherein said LASM is essentially homogeneously dispersed throughout said media prior to reaction with said amplified target analyte units.

14. A method for determining the presence or absence of two or more target nucleotide sequences hereinafter referred to as target analytes, in a specimen sample, said method comprising the steps of:

a) providing a specimen sample to be analyzed;

b) providing a testing media suitable for specimen sample introduction, said testing media containing target analyte-amplification materials which are essentially homogeneously distributed throughout said media and are selectively specific to each of said target analytes;

c) releasing any of said target analytes from target organisms which may be contained in the specimen sample;

d) reacting any released target analytes with said target analyte-amplification materials in said media so as to form essentially immobile amplified colonies of said target analytes in said media; and e) reacting any amplified target analyte units in said colonies with labeled analyte-specific materials (LASMs) which are substantially homogeneously distributed throughout said testing media and which can migrate through said testing media, said detectable substance being operable to selectively bind with any target analytes in colonies thereof which form in said media so as to differentially highlight said formed target analyte colonies from the remainder of said media, whereby any amplified target analyte colonies which consist of one of said target analytes will be differentially highlighted from amplified target analyte colonies which consist of another of said target analytes.

15. The method of claim 14 wherein said LASMs comprise respective differentially labeled artificial nucleotide sequences which are complementary to respective sequences of said target analytes.

16. A method for quantifying a target nucleotide sequence hereinafter referred to as target analyte, in a specimen sample, said method comprising the steps of:

a) providing a fixed volume of a specimen sample to be analyzed;

b) providing a testing media suitable for specimen sample introduction, said testing media containing target analyte-specific amplification materials which are essentially homogeneously; distributed throughout said media;

c) releasing any of said target analyte from target life forms which may be contained in said fixed volume specimen sample;

d) reacting any released target analyte with said target analyte-specific amplification material in said media so as to form essentially immobile amplified colonies of said target analyte in said media;

e) reacting any amplified target analyte units with a labeled analyte-specific material (LASM) which is substantially homogeneously distributed throughout said testing media and which can migrate through said testing media, said detectable substance being operable to bind with target analyte units in any formed target analyte colonies in said media so as to form differentially highlighted target analyte colony areas in said media; and f) counting the number of highlighted amplified target analyte colony areas in the media so as to obtain a target analyte-per-unit-volume sample concentration.

17. The method of claim 16 comprising the step of determining the percentage of amplified colonies of nucleic acid sequences in the sample and/or the percentage of in situ lysed organisms or cells in the sample that contain said target analyte.

18. A method for quantifying two or more target nucleotide sequences hereinafter referred to as target analytes, in a specimen sample, said method comprising the steps of:

a) providing a fixed volume of a specimen sample to be analyzed;

b) providing a testing media suitable for specimen sample introduction, said testing media containing target analyte-specific amplification materials which are essentially homogeneously distributed throughout said media;

c) releasing any of said target analytes from target life forms which may be contained in said fixed volume specimen sample;

d) reacting any released target analytes with said sequence-amplification materials in said media so as to form essentially immobile amplified colonies of said target analytes in said media; and e) reacting any amplified target analyte units in said colonies with labeled analyte-specific materials (LASMs) which are substantially homogeneously distributed throughout said testing media and which can migrate through said testing media, said LASMs being operable to selectively bind with any amplified target analyte units which form in said media so as to differentially highlight said amplified target analyte colonies from the remainder of said media, whereby any amplified target analyte colonies which consist of one of said target analytes will be differentially highlighted from amplified colonies which consist of another of said target analytes; and f) counting the number of each of the differentially highlighted amplified target analyte colony areas in the media so as to obtain target analyte-per-unit-volume sample concentrations of each of the target analytes which appear in the media.

19. A method for determining the presence or absence of a target nucleotide sequence, hereinafter referred to as target analyte, in a specimen sample, said method comprising the steps of:

a) providing a specimen sample to be analyzed, said specimen sample being suspected of containing free target analyte;

b) providing a testing media suitable for specimen sample introduction, said testing media containing target analyte-specific amplification materials which are essentially homogeneously distributed throughout said media;

c) reacting any free target analyte with said target analyte-specific amplification material in said media so as to form essentially immobile amplified colonies of said target analyte in said media; and e) reacting any target analyte with a labeled analyte-specific material (LASM) which is substantially homogeneously distributed throughout said testing media and which can migrate through said testing media, said LASM being operable to bind with amplified target analyte units in any formed target analyte colonies in said media so as to differentially highlight said target analyte colonies from the remainder of said media.

20. A method for determining the presence or absence of two or more target nucleotide sequences, hereinafter referred to as target analytes, in a specimen sample, said method comprising the steps of:

a) providing a specimen sample to be analyzed, said specimen sample being suspected of containing free target analytes;

b) providing a testing media suitable for specimen sample introduction, said testing media containing target analyte-amplification materials which are selectively specific to each of said target analytes which are essentially homogeneously distributed throughout said media;

c) reacting any free target analytes with said target analyte-amplification materials in said media so as to form essentially immobile amplified colonies of said target analytes in said media; and d) reacting any amplified target analyte units in said colonies with labeled analyte-specific materials (LASMs) which are substantially homogeneously distributed throughout said testing media and which can migrate through said testing media, said LASMs being operable to selectively bind with any target analytes in any colonies thereof which form in said media so as to differentially highlight said formed target analyte colonies from the remainder of said media, whereby any amplified target analyte colonies which consist of one of said target analytes will be differentially highlighted from amplified target analyte colonies which consist of another of said target analytes.

21. A method for quantifying a target nucleotide sequence hereinafter referred to as target analyte, in a specimen sample, said method comprising the steps of:

a) providing a specimen sample to be analyzed, said specimen sample being suspected of containing free target analyte;

b) providing a testing media suitable for specimen sample introduction, said testing media containing target analyte-specific amplification materials which are essentually homogeneously disribusted said media;

c) reacting any free target analyte with said target analyte-specific amplification material in said media so as to form essentially immobile amplified colonies of said target analyte in said media;

e) reacting any amplified target analyte units with a labeled analyte-specific material (LASM) which is substantially homogeneously distributed throughout said testing media and which can migrate through said testing media, said LASM being operable to bind with target analyte units in any formed target analyte colonies in said media so as to form differentially highlighted target analyte colony areas in said media; and f) counting the number of highlighted amplified target analyte colony areas in the media so as to obtain a target analyte-per-unit-volume sample concentration.

22. An assembly for determining the presence or absence of a target nucleotide sequence analyte hereinafter referred to as target analyte, in a specimen sample, said assembly comprising:

a) a media into which the specimen sample can be introduced, and which is operable to support amplification of the target analyte to an extent needed to produce colonies thereof while limiting migration of any amplified target analyte colonies which are formed within the media;

b) target analyte-specific amplification reagents which are essentially homogeneously distributed throughout said media, said amplification reagents being operable to selectively amplify and form colonies of any of the target analyte which may be present in the specimen sample; and c) a detectable substance which is essentially homogeneously distributed throughout the media and which will bind to said target analyte, said substance being capable of migrating through said media to an extent necessary to differentially highlight any amplified target analyte colonies which may be formed in said media.

23. A method for determining the presence or absence of a target nucleotide sequence hereinafter referred to as target analyte, in a specimen sample, said method comprising the steps of:

a) providing a specimen sample to be analyzed;

b) providing a testing media suitable for specimen sample introduction, said testing media containing target analyte-specific amplification materials which are essentially homogeneously distributed throughout said media;

c) releasing any of said target analyte from target organisms which may be contained in the specimen sample;

d) reacting any released target analyte with said target analyte-amplification material in said media so as to form essentially immobile amplified colonies of said target analyte in said media; and e) reacting any released target analyte with a detectable substance, which is substantially homogeneously distributed throughout said testing media and which can migrate through said testing media, said detectable substance being operable to bind with amplified target analyte units in any formed target analyte colonies in said media so as to differentially highlight said target analyte colonies from the remainder of said media.

24. A method for determining the presence or absence of a target nucleotide sequence hereinafter referred to as target analyte, in a specimen sample, said method comprising the steps of:

a) providing a specimen sample to be analyzed, said specimen sample being suspected of containing free target analyte;

b) providing a testing media suitable for specimen sample introduction, said testing media containing target analyte-specific amplification materials which are essentially homogeneously distributed throughout said media;

c) reacting any free target analyte with said target analyte-specific amplification material in said media so as to form essentially immobile amplified colonies of said target analyte in said media; and e) reacting any target analyte with a detectable substance, which is substantially homogeneously distributed throughout said testing media and which can migrate through said testing media, said detectable substance being operable to bind with amplified target analyte units in any formed target analyte colonies in said media so as to differentially highlight said target analyte colonies from the remainder of said media.

* * * * *

UNITED STATES PATENT AND TRADEMARK OFFICE
CERTIFICATE OF CORRECTION

PATENT NO. : 6,007,990

DATED: : December 28, 1999

INVENTOR(S): Robert A. Levine, et al.

It is certified that errors appear in the above-identified patent and that said Letters Patent is hereby corrected as shown below.

In Col, 19, Line 7, "detectable substance" should read "LASM".
In Col, 19 Lines 36 and 37, "detectable substance" should read "LASM".
In Col, 20, Line 5, "detectable substance" should read "LASM".

Signed and Sealed this

Twenty-seventh Day of March, 2001

Attest:

NICHOLAS P. GODICI

Attesting Officer

Acting Director of the United States Patent and Trademark Office